United States Patent [19]

Anderson et al.

[11] 4,052,508

[45] Oct. 4, 1977

[54] HETEROCYCLIC DIHYDROANTHRACEN IMINES

[75] Inventors: Paul S. Anderson, Lansdale; Marcia E. Christy, Perkasie; Gerald S. Ponticello, Lansdale, all of Pa.

[73] Assignee: Merck & Co., Inc., Rahway, N.J.

[21] Appl. No.: 564,012

[22] Filed: Apr. 7, 1975

Related U.S. Application Data

[63] Continuation-in-part of Ser. No. 498,484, Aug. 19, 1974, abandoned.

[51] Int. Cl.$^2$ .............. C07D 471/08; A61K 31/395; C07D 487/08
[52] U.S. Cl. .................. 424/258; 260/250 AC; 260/256.4 F; 260/256.5 R; 260/283 SC; 260/283 S; 260/287 B; 260/288 CF; 260/325 R; 260/326.1; 424/250; 424/251; 424/273 R; 548/304; 548/326; 548/305; 548/306; 548/323
[58] Field of Search ......... 260/288 CF, 287 B, 283 S; 424/258

[56] References Cited

U.S. PATENT DOCUMENTS 3,678,072  7/1972  Klanderman et al. ........ 260/326.5 B

OTHER PUBLICATIONS

Wittig et al., Annelen, vol. 630, pp. 10–18 (1960).
BoVaris et al., J. Chem. Soc. Chem. Comm., vol. 1974, p. 870.
Heaney et al., Chem. Abstr., vol. 77, col. 164364n (1972).
Kricha et al., J. Chem. Soc. Perkin I, vol. 1973 pp. 766–771.
Emmet et al., Tetrahedron, vol. 22, pp. 1011–1018 (1966).
Harrison et al., Tetrahedron, vol. 24, pp. 4589–4594 (1968).

*Primary Examiner*—Donald G. Daus
*Assistant Examiner*—Mary C. Vaughn
*Attorney, Agent, or Firm*—William H. Nicholson; Harry E. Westlake, Jr.

[57] ABSTRACT

Heterocyclic dihydroanthracen imines are disclosed to be useful as minor tranquilizers, anticonvulsants, muscle relaxants and to be useful in the treatment of extrapyramidal disorders such as Parkinson's disease; also disclosed are processes for the preparation of such compounds; pharmaceutical compositions comprising such compounds; and methods of treatment comprising administering such compounds and compositions.

7 Claims, No Drawings

HETEROCYCLIC DIHYDROANTHRACEN IMINES

This application is a continuation-in-part of co-pending application Ser. No. 498,484, filed Aug. 19, 1974, now abandoned.

BACKGROUND OF THE INVENTION

This invention relates to certain heterocyclic dihydroanthracen imines; substituted derivatives and pharmaceutically acceptable salt, ester, and amide derivatives thereof which are useful as minor tranquilizers, anticonvulsants, muscle relaxants and useful in the treatment of extrapyramidal disorders such as Parkinson's disease. For convenience the compounds of this invention will hereinafter collectively be referred to as "heterocyclic anthracenimines."

This invention also relates to processes for the preparation of such heterocyclic anthracenimines, to pharmaceutical compositions comprising such compounds, and to methods of treatment comprising administering such compounds and compositions.

The compounds of the present invention may generically be represented by the following structural formula:

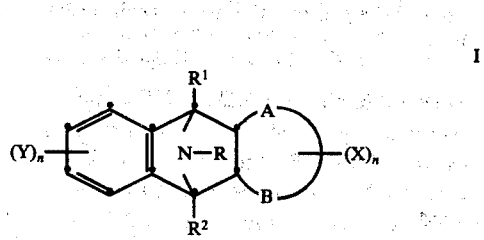

wherein
R is hydrogen, acyl, aryl, alkoxycarbonyl, alkyl, aralkyl, alkylcycloalkyl, cycloalkyl, alkenyl, dialkylaminoalkyl, hydroxyalkyl, alkynyl, or trialkylsilyl;
$R^1$ and $R^2$ are independently selected from the group consisting of hydrogen, alkyl, haloalkyl, aralkyl, aryl, alkenyl, and dialkylaminoalkyl;
X and Y are selected from the group consisting of halogen such as chloro, fluoro, bromo, iodo and the like, alkoxy, alkyl, dialkylaminoalkyl, carboxamido, haloalkyl, haloalkylthio, allyl, aralkyl, cycloalkyl, aralkoxy, aryl, substituted aryl, alkylthio, alkylsulfonyl, haloalkylsulfonyl, alkylsufinyl, haloalkylsulfinyl, arylthio, haloalkoxy, amino, aminoalkyl, alkylamino, dialkylamino, hydroxy, carbamoyl, N-alkyl-carbamoyl, N,N-dialkylcarbamoyl, and dialkylsulfamoyl;
n is an integer selected from 0 (X or Y is hydrogen) 1, 2, 3, or 4;

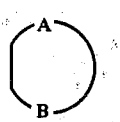

represents an unsaturated heterocyclic or heteropolycyclic moiety wherein the heteroatoms A and B are selected from O, N and NR wherein R is as defined above.

Thus, it is an object of the present invention to provide heterocyclic anthracenimines of the above general description (I). It is also an object of this invention to provide pharmaceutical compositions comprising such heterocyclic anthracenimines and their non-toxic, pharmaceutically acceptable salt, ester and amide derivatives. Lastly, it is an object of the present invention to provide methods of treatment comprising administering the compounds and compositions of the present invention in situations where a minor tranquilizer and/or muscle relaxant and/or anticonvulsant effect is indicated or in the treatment of extrapyramidal disorders such as Parkinson's disease.

DETAILED DESCRIPTION OF THE INVENTION

With respect to the heterocyclic anthracenimines of the present invention (Structure I, above-depicted), the preferred embodiments are those wherein:

$R^1$ and $R^2$ are independently selected from the group consisting of hydrogen, lower alkyl, and halo lower alkyl having from 1 to about 6 carbon atoms, and dialkylaminoalkyl having from 3 to about 15 carbon atoms;

R is hydrogen or lower alkyl having from about 1 to about 6 carbon atoms, cycloalkyl having from 3 to about 6 carbon atoms, benzyl and substituted benzyl, or dialkylaminoalkyl having from 3 to about 15 carbon atoms;

Y and X are selected from the group consisting of lower alkyl having from 1 to about 6 carbon atoms, iodo, chloro, bromo, lower alkoxy having from 1 to about 6 carbon atoms, halo-substituted lower alkoxy having from 1 to about 6 carbon atoms, halo lower alkyl having from 1 to about 6 carbon atoms, hydroxy, carboxamido, lower alkylthio and aminoalkyl;

n is an integer selected from 0 (X or Y is hydrogen) 1, 2, 3, or 4.

The most preferred heterocyclic anthracenimine embodiments of the present invention are those represented by species structures II, III, IV, IVa, V, VI, VII, VIII, and IX:

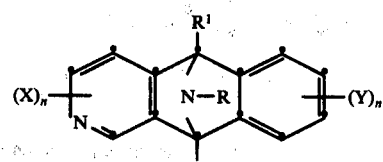

II

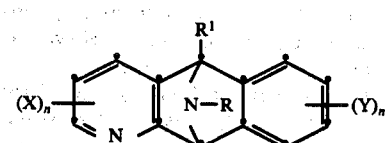

III

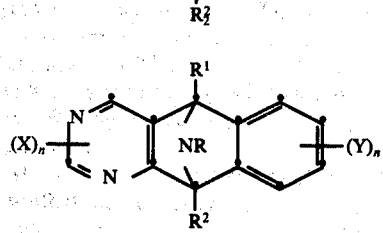

IV

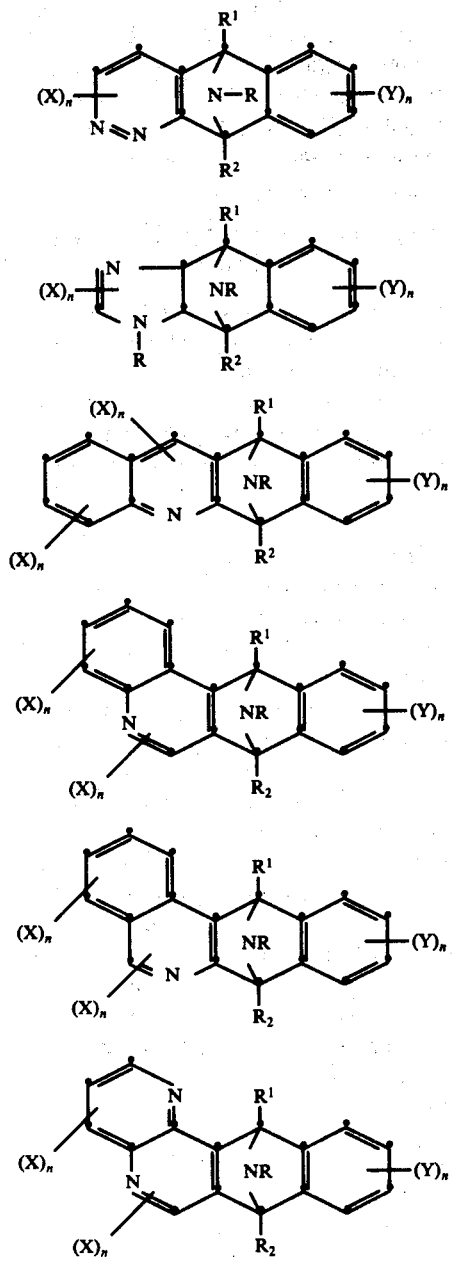

wherein
R¹ and R₂ are selected from the group consisting of hydrogen, lower alkyl having from 1 to about 6 carbon atoms, trifluoromethylsulfonyl, trifluoromethyl, diloweralkylamino lower alkyl, such as dimethylaminopropyl and the like;

R is hydrogen or lower alkyl having from 1 to about 6 carbon atoms, benzyl, substituted benzyl, dimethylaminopropyl, cyclopropyl, or cyclobutyl;

X and Y are iodo, chloro, bromo, lower alkoxy having from 1 to about 6 carbon atoms, lower alkyl having from 1 to about 6 carbon atoms, carboxamido, trifluoromethoxy, thiomethyl, trifluoromethyl, trifluoromethylsulfonyl, and trifluoromethylthio;

n is an integer selected from 0 (X or Y is hydrogen), 1, 2, 3 or 4.

In general, the anthracenimines of the present invention are prepared by reacting an appropriately substituted hetaryne (Ia) with an appropriately substituted isoindole (IIa) according to the following reaction:

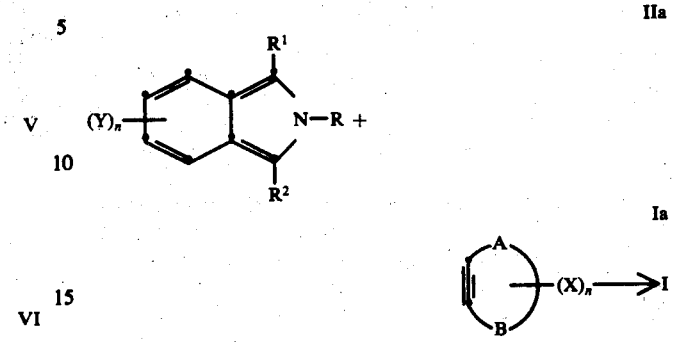

wherein all substituents are as previously defined.

As a practical matter the hetaryne reactant is generated in situ under conditions compatible with the ultimate Diels-Alder condensation with the isoindole. Preparation of such reactants and process conditions for the ultimate preparation of the heterocyclic anthracenimines of the present invention are described hereinafter.

ISOINDOLE PREPARATION

The isoindole intermediates disclosed in copending, commonly assigned U.S. Pat. application Ser. No. 564,011 of Paul S. Anderson, Marcia E. Christy and Gerald S. Ponticello (Merck & Co., Inc., filed concurrently, which is a continuation-in-part of U.S. Pat. application Ser. No. 470,093, filed May 15, 1974 now abandoned) are also useful in the preparation of the instant compounds and therefore said application is incorporated by reference.

Many of the isoindoles useful in preparation of the heterocyclic anthracenimines of the present invention are known and readily available. Alternately, such isoindoles may be readily prepared by reacting an ortho-disubstituted benzene with a halogenating agent, such as N-bromosuccinimide (NBS), followed by reaction of the resulting α,α'-dihalogenated product with an N-substituted hydrazine (RNHNH₂); treatment of the latter with base provides the desired isoindol (Ia):

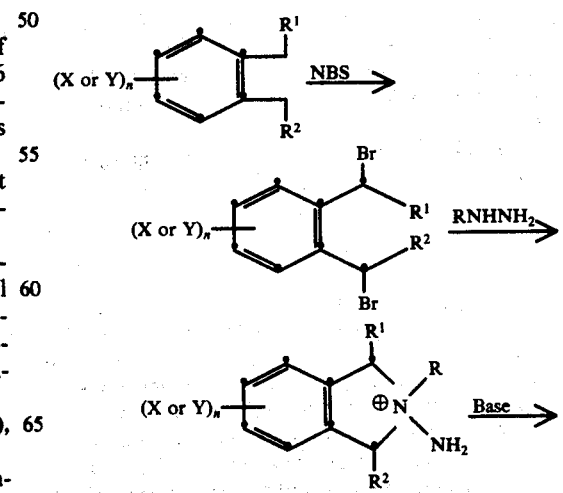

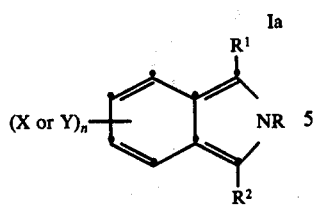

wherein all substitutes are as previously defined.

Typically, the halogenating step in the preparation of the isoindole is conducted in the presence of an initiator such as benzoyl peroxide and the like under ultra violet irradiation. There is no criticality as to the reaction temperature, solvent system or the base used in the final step. Suitable solvents for the reaction include hydrocarbons such as hexane, benzene, and the like and halohydrocarbons such as carbontetrachloride, chlorobenzene and the like. Typically the reaction temperature is from about 25° C. to the reflux temperature; the noncritical base may be selected from sodium hydroxide, potassium hydroxide, potassium carbonate, and the like.

Another method of preparing suitably substituted isoindoles is set forth in the following scheme:

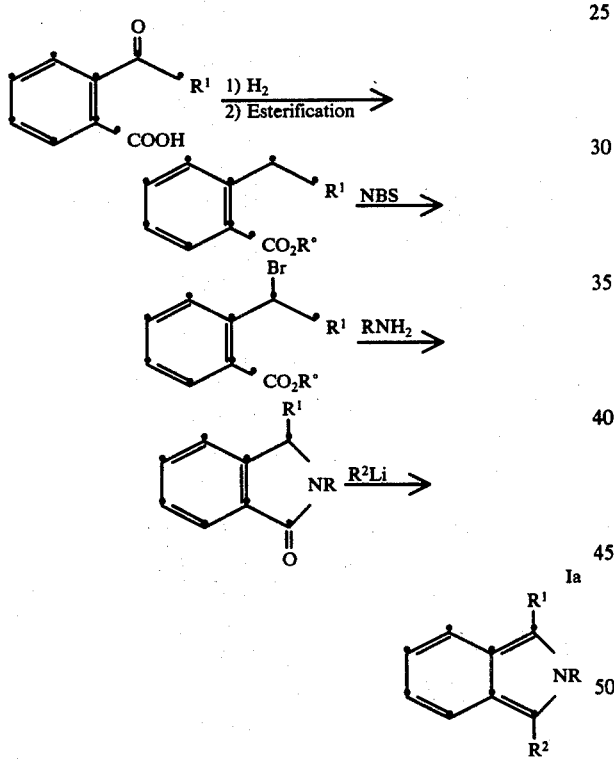

wherein all symbols have previously been defined and R° is any lower alkyl moiety such as methyl, ethyl, propyl, and the like. According to the above process, the o-acylbenzoic acid is first hydrogenated to reduce the carbonyl group by conventional procedures such as hydrogenation over Pd/C in aqueous sodium hydroxide solution. thereafter the free carboxy group is esterified by treating with diazomethane, sulfuric acid in methanol or Hcl in ethanol or other standard methods. Halogenation of the resulting substituted benzoic acid ester provides the above-illustrated α-halo intermediate. The halogenation may be effected, for example, by treating the ester with N-bromosuccinamide in carbon tetrachloride at reflux. The treatment of the α-halo intermediate with the primary amine, RNH$_2$, in methanol, ethanol, acetonitrile, ether, THF or other polar organic solvent provides the above-illustrated phthalimidine which on treatment with R$^2$Li in ether, benzene, THF or other non-participating organic solvent at reflux or with a Grignard reagent, R$^2$MgX (X is halo such as chloro, bromo, or iodo) in anisole, THF, glyme or dibutyl ether at reflux provides the desired isoindole (Ia). Relative to the process is illustrated immediately above, the esterification step may be eliminated according to the following procedure:

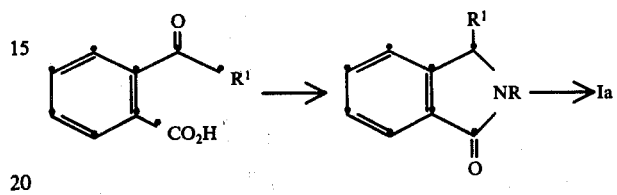

wherein the phthalimidine intermediate is obtained directly by treating the ortho-acylbenzoic acid with the primary amine, RNH$_2$, in the presence of NaCNBH$_3$ when protic solvents such as methanol, ethanol, and the like are employed or in the presence of NaBH$_4$, MgSO$_4$ and the hydrochloride of the primary amine when a polar aprotic solvent such as acetonitrile DMF, HMPA, and the like are employed. In either of the solvent systems there is no undue criticality as to reaction temperature, time and ratio of reactants; however, the following conditions are typically employed when the aprotic system is employed; the primary amine, as an equimolar mixture of the free base and its acid addition salt, is present in excess relative to the acylbenzoic acid, and the sodium borohydride is added portionwise over several hours to the solution of the amine and the acylbenzoic acid - MgSO$_4$ slurry.

Another method for preparing the above-mentioned isoindoles involves treating an ortho-diacylbenzene with a primary amine, RNH$_2$, in the presence of a reducing agent such as NaBH$_4$ or the like in a protic solvent at a reaction temperature of 20°-35° C according to the following reaction scheme (all symbols are as previously defined):

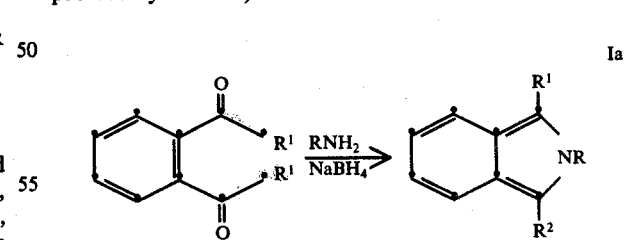

Another method for preparing the above-described isoindoles when either R$^1$ or R$^2$ is hydrogen involves treating phthalic anhydride with the primary amine, RNH$_2$, to yield a phthalimide intermediate which on reduction with, for example, zinc dust in glacial acetic acid yields the phthalimidine which on treatment with an appropriate lithium alkyl, LiR$^2$, or Grignard reagent, R$^2$MgX, yields the desired isoindole according the following scheme:

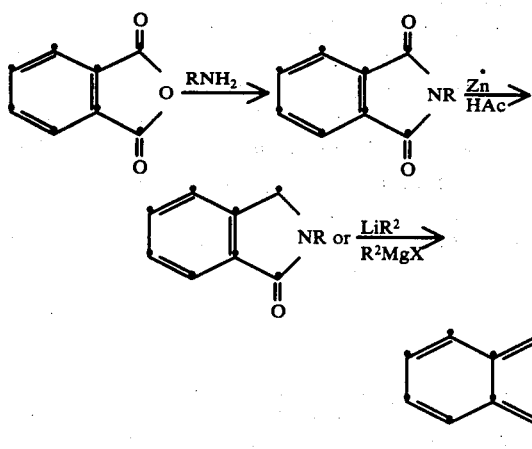

Yet another procedure for preparing the above-described isoindoles, especially when either $R^1$ or $R^2$ is hydrogen and when the benzoid nucleus of the isoindole bears an electron releasing substituent (here denoted X' which is selected from the group classed under X and Y, previously defined), such as alkyl or halogen or the like involves Friedel-Crafts alkylation of a meta - X' substituted benzoic acid. The following equation summarizes this approach:

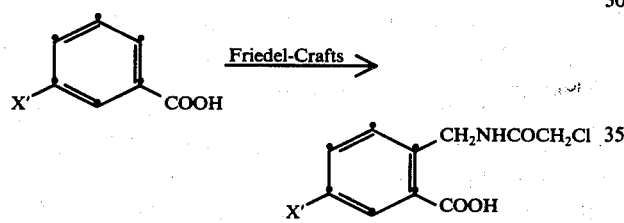

The immediate Friedel-Crafts product spontaneously cyclizes to form the phthalimidine intermediate which may be N-alkylated by treating with RI in the presence of sodium hydride in a solvent system such as DMF or a 1:1 mixture of dimethylformamide and benzene. The resulting N-substituted phthalimidine on treatment with a suitable lithium alkyl ($LiR^1$) or Grignard reagent ($R^1MgX$) as previously defined, yields the desired $R^1$ or $R^2$ substituted isoindole having the X' substituted in the 5-position:

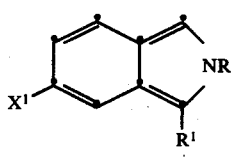

Suitable Friedel-Crafts reagents for the above reaction may be selected from N-hydroxymethylchloroacetamide and N-hydroxymethylphthalimide. The preferred Friedel-Crafts catalyst is concentrated $H_2SO_4$. Typically, the reaction is conducted neat or in solvents such as $H_2SO_4$ and the like at a temperature of from about 0° C. to about 30° C.

Those skilled in the art will recognize that the above-disclosed processes may be employed individually or may be hybridized according to the most convenient path in the synthesis of the isoindoles needed for the preparation of the heterocyclic anthracenimines of the present invention.

PREPARATION OF THE HETARYNE REACTANT

The transient hetaryne reactant may be prepared by a variety of means including flash photolysis of a nuclear substituted heterocycle or by treatment of an ortho-dihalo substituted heterocycle or monohalo-substituted heterocycle with a strong base; the operation upon pyridine is representative:

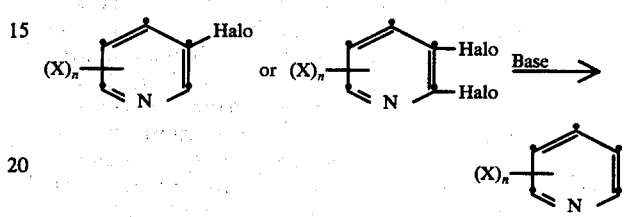

For purposes of the present invention it is preferred that the hetaryne reactant be generated in situ for immediate Diels-Alder condensation with the isoindole. The following equation illustrates this reaction:

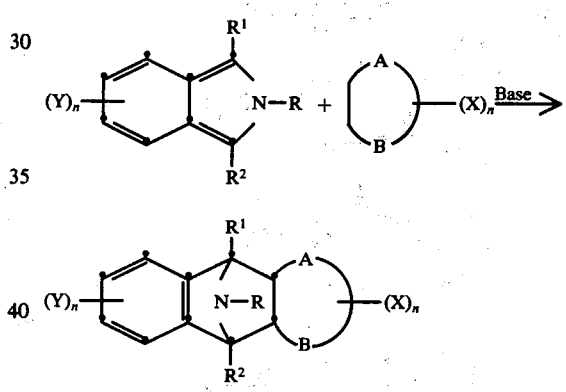

Suitable bases for the above reaction may be selected from the group consisting of alkali and alkaline earth metals and their corresponding oxides, hydrous oxides, alkoxides, alkali metal amides, alkali metal alkyls and the like. The most preferred bases are magnesium metal, and alkali metal alkyl such as methyllithium, butyllithium, phenyllithium, and alkali metal amides such as sodium amide, lithium diisopropylamide, lithium 2,3,6,6-tetramethylpiperidide and the like. There is no undue criticality as to the identity of the reaction solvent and suitable solvents may be selected from hydrocarbons such as benzene, hexane, cyclohexane and the like, oxygenated solvents such as ether, dioxane, tetrahydrofuran, anisole and the like. Typically the reaction is conducted at from about −70° C. to the reflux temperature.

A second method for the preparation of the heterocyclic anthracenimines of the present invention involves derivatization operations upon the basic heterocyclic anthracenimine nucleus to provide certain embodiments of the present invention. The following reaction is illustrative of this approach:

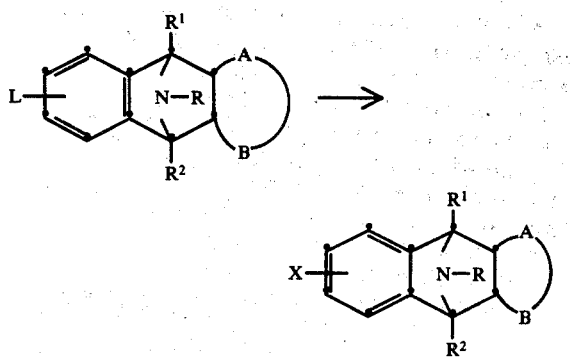

wherein for purposes of illustration the parent compound is shown to be substituted only with the functional group L; however, it is not critical or even preferred that L be the sole nuclear substituent for this aspect of the invention. L may be any chemically modifiable group such as hydroxy, bromo, iodo, chloro and the like, which may be transformed to the function X by well known procedures. X is as previously defined and, especially for this aspect of the invention, embraces radicals such as cyano, trifluoromethylthio, methylthio, and the like. Suitable solvents for this process aspect of the invention include dimethylformamide, hexamethylphosphoramide (HMPT), ether, THF and the like. Typically the reaction is conducted at from about 25° C. to the reflux temperature.

Also included within the scope of the present invention are non-toxic pharmaceutically acceptable salt, ester and amide derivatives of I. Acid addition salts are preferred. Such acid addition salts of the heterocyclic anthracenimine compounds are formed by mixing a solution of the heterocyclic anthracenimine compound with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid and the like.

In the method of treatment aspect of the present invention, the instant minor tranquilizer heterocyclic anthracenimines are capable of producing anxiety relief without causing excessive sedation or sleep at a unit dosage level of from about 0.1 to about 500 mg. per kilogram of body weight, or at a daily dosage level of from about 0.4 to about 2,000 mg. per kilogram of body weight. In addition, the heterocyclic anthracenimines of the present invention are useful as muscle relaxants and anticonvulsants and in the treatment of extrapyramidal disorders when indicated at comparable dosage levels. Of course, it is understood that the exact treatment level will depend upon the case history of the animal or human individual being treated and in the last analysis the precise treatment level falling within the above guidelines is at the discretion of the therapist.

Also included within the scope of the present invention ae pharmaceutical compositions comprising such heterocyclic anthracenimines. Preferable these compositions are in unit dosage forms such as tablets, pills, capsules, powders, granules, sterile parenteral solutions or suspensions, and the like. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of a heterocyclic anthracenimine of the present invention, or a non-toxic pharmaceutically acceptable salt, ester or amide derivative thereof. When referring to these preformulation compositions as homogeneous, it is meant that the active ingredient, i.e., the heterocyclic anthracenimine, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action of the instant heterocyclic anthracenimines. For example, the tablet or pill can comprise an inner dosage and an outer dosage component, the latter being in the form of an envelope over the former. The two components can be separated by an enteric layer which serves to resist disintegration in the stomach and permits the inner component to pass intact into duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The phararmaceutical heterocyclic anthracenimine formulations of the present invention can be administered orally, parenterally, or rectally. Orally, they may be administered in tablets, capsules, suspensions or syrups, the preferred dosage form being a compressed tablet containing from 0.1 to about 500 mg. of the active ingredient. The optimum dosage depends of course on the dosage form being used and the type and severity of the condition being treated. In any specific case, as previously mentioned, the appropriate dosage selected will further depend on factor of the patient which may influence response to the drug, for example, general health, age, weight, and the desired effect.

The following examples representatively illustrate, but do not limit, the product, process, method of treatment, or compositional aspects of the present invention.

EXAMPLE 1

1-Aza-5,10-dihydro-11-methylanthracen-5,10-imine

Ethylether (30 ml.) and 1.9 molar butyllithium in hexane (12 ml.) are added to a dry flask under $N_2$ and cooled to −70° C. in a dry ice/acetone bath. To this is added dropwise with stirring a solution of 4.0 g. of 3-bromo-2-chloropyridine in ether (20 ml.) followed by a solution of 4.0 g. of N-methylisoindole in ether (80 ml.), and the mixture is stirred at −70° C. for 5 min.

Thereafter the reaction mixture is quickly warmed to 20° C. and allowed to stir overnight at 25° C. The reaction mixture is poured into water and extracted with chloroform (3 × 100 ml.). The combined chloroform extracts are dried over $Na_2SO_4$, filtered and concentrated under reduced pressure. The residue is chromatographed on silica-gel eluting with 2% methylalcohol/-chloroform. The crude product obtained from the eluent is treated with fumaric acid in isopropanol to obtain the fumaric acid salt, m.p. 168°–170° C., after recrystallization from isopropanol-ethylacetate (1:1).

Elemental analysis for $C_{14}H_{12}N_2\cdot 2C_4H_4O_4$
Calcd.: C, 60.0; H, 4.54; N, 6.35.
Found: C, 60.15; H, 4.70; N, 6.43.

EXAMPLE 2

2-Aza-5,10-dihydro-11-methylanthracen-5,10-imine

Ethyl ether (30 ml.) and 1.9 molar butyllithium in hexane (12 ml.) are added to a dry flask under $N_2$ and cooled to −70° C in a dry ice/acetone bath. To this is added dropwise with stirring a solution of 4 g. of 4-bromo-3-chloropyridine in ether (30 ml.) followed by a solution of 4.0 g. of N-methylisoindole in ether (60 ml.). After complete addition the mixture is stirred at −70° C. for 5 min. and then the reaction mixture is quickly warmed to 20° C. and allowed to stir overnight at 25° C. The reaction mixture is poured into water and extracted with chloroform (3 × 100 ml.). The combined chloroform extracts are dried over $Na_2SO_4$, filtered and concentrated under reduced pressure. The residue is chromatographed on silica gel eluting with 4% $CH_3OH/CHCl_3$. The crude product obtained from the eluent is treated with fumaric acid in isopropanol to obtain the fumaric acid salt, m.p. 149°–151° C., after recrystallization from isopropanol-ethylacetate (1:1).

Elemental analysis for $C_{14}H_{12}N_2\cdot 1.5C_4H_4O_4$:
Calcd.: C, 62.60; H, 4.75; N, 7.30.
Found: C, 62.43; H, 5.09; N, 6.93.

Following the procedure of Example 2, 2-aza-5,10-dihydro-5,10,11-trimethylanthracen-5,10-imine is prepared when an equivalent quantity of 1,2,3-trimethylisoindole is substituted for the N-methylisoindole of Example 2.

EXAMPLE 3

1-Aza-5,10-dihydro-5,10,11-trimethylanthracen-5,10-imine

In a dry apparatus maintained in a nitrogen atmosphere, a solution of 19.5 ml. of 2.2 M. n-butyllithium in hexane and 30 ml. of absolute ether is stirred and cooled to −70° C. in a dry ice-acetone bath. To this is added dropwise a solution of 8.15 g. (0.0424 mole) of 3-bromo-2-chloropyrindine in 40 ml. of absolute ether followed by a solution of 6.15 g. (0.0386 mole) of 1,2,3-trimethylisoindole in 60 ml. of absolute ether. After the addition is complete, the mixture is warmed rapidly to 20° C. and allowed to stir overnight at 25° C. The reaction mixture is hydrolyzed by the dropwise addition of water. The ether layer is separated, filtered, washed and dried. Evaporation under reduced pressure leaves a dark oily residue that is triturated with hexane and filtered from insoluble material. Evaporation of the filtrate under reduced pressure leaves 3.09 g. of the crude product as the residual dark oil. Purification is effected by column chromatography on 200 g. of alumina (Activity I), the product being eluted with methanol-chloroform (1:1). Fraction containing a major component of $R_f$ 0.2 on a fluorescent silica thin layer plate developed with 1% methanol/chloroform are combined. Evaporation of the solvent under reduced pressure leaves the product as an amber oil in 6% yield.

The base is converted to the hydrogen oxalate salt by treating a solution in 95% ethanol containing a few drops of water with oxalic acid in 95% ethanol. Dilution with absolute ether precipitates the salt that is recrystallized twice from acetone to obtain off-white crystals, m.p. 178°–179° C.

Elemental analysis for $C_{16}H_{16}N_2\cdot C_2H_2O_4$.
Calcd.: C, 66.24; H, 5.56; N, 8.58.
Found: C, 66.13; H, 5.54; N, 8.44.

EXAMPLE 4

Preparation of 1,2,3-trimethylisoindole

A mixture of 50 g. (0.374 mole) of o-diethylbenzene, 146 g. (0.822 mole) of N-bromosuccinimide, 0.1 g. of benzoyl peroxide, and 800 ml. of carbon tetrachloride is heated under reflux with stirring and ultraviolet irradiation until the reaction is complete. The precipitated succinimide is filtered, washed with carbon tetrachloride, and the filtrate is evaporated to dryness under reduced pressure. The residual $\alpha,\alpha'$-dibromo-o-diethylbenzene is dissolved in 800 ml. of absolute ether. To the stirred solution under nitrogen is added dropwise a solution of 40 g. (0.87 mole) of methyl hydrazine in 50 ml. of absolute ether. A gummy precipitate separates. After 3 hours of stirring and an overnight period of standing, the ether is decanted. The residue dissolved in 625 ml. of water is treated with 375 ml. of 40% sodium hydroxide solution and the mixture is stirred at reflux for 1.5 hours. After cooling, the preicipitate of the crude product is collected, washed with water, and dissolved in 600 ml. of ether. The ether solution is washed repeatedly with water and dried over anhydrous magnesium sulfate with stirring and cooling in an ice bath. The filtered solution is evaporated under reduced pressure and the residual dark yellow solid is triturated with petroleum ether, filtered and dried in vacuo to yield 15.56 g. of 1,2,3-trimethyl-isoindole.

EXAMPLE 5

Preparation of 5-fluoro-2-methylisoindole

Following the procedure described in Example 4 3,4-dimethylfluorobenzene is converted to 5-fluoro-2-methylisoindole. The crude, dark oily product is purified by short path distillation in vacuo. The yellow oily solid distillate, b.p. 90°–100° C./1mm. Hg., is sublimed at 65° C. and 0.4 mm. Hg. to yield slightly oily yellow crystals of 5-fluoro-2-methylisoindole, m.p. 60–65° C.

EXAMPLE 6

Preparation of 5-bromo-1,2,3-trimethylisoindole

Following the procedure described in Example 4 3,4-diethylbromobenzene is converted to 5-bromo-1,2,3-trimethylisoindole. The crude solid 5-bromo-1,2,3-trimethylisoindole is purified by sublimation at 95°–100° C. and 0.05 mm. Hg. to yield yellow crystals.

EXAMPLE 7

1,3-Diaza-5,10-dihydro-11-methylanthracen-5,10-imine

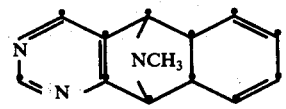

In a dry apparatus maintained in a nitrogen atmosphere, 1.8 molar methyllithium in ether (11.7 ml.) is added dropwise to a stirred solution of 2.82 g. (0.02 mole) of 2,2,6,6-tetramethylpiperidine in 15 ml. of dry tetrahydrofuran. The resulting solution is added dropwise to a stirred solution of 2.62 g. (0.02 mole) of N-methyl-isoindole and 2.05 g. (0.02 mole) of 5-chloropyrimidine in 20 ml. of dry tetrahydrofuran. After an overnight period at reflux, the mixture is poured into a saturated ammonium chloride solution containing 3% of concentrated ammonium hydroxide. The tetrahydrofuran layer is separated and concentrated under reduced pressure. The residue is chromatographed on silica gel, eluting with 5% methanol/chloroform, to obtain the purified product as the residue from evaporation of the eluant.

When the N-methylisoindole of Example 7 is replaced by an equivalent amount of 1,2,3-trimethylisoindole; 5-bromo-1,2,3-trimethylisoindole; and 5-iodo-1,2,3-trimethylisoindole, respectively, there is obtained 1,3-diaza-5,10-dihydro-5,10,11-trimethyl-anthracen-5,10-imine; (6- and 7-)bromo- and iodo-1,3-diaza-1,5-dihydro-5,10,11-trimethyl-anthracen-5,10-imine, respectively, Similarly, when the 5-chloropyrimidine of Example 7 is replaced by an equivalent amount of 5-chloro-1,2-diazine, there is obtained 1,2-diaza-11-methyl-5,10-dihydroanthracen-5,10-imine.

EXAMPLE 8

1,10-Dimethyl-4,9-dihydro-1H-naphth(2,3-d)imidazol-4,9-imine

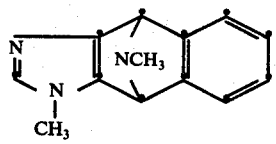

Following the procedure described in Example 7, 1,10-dimethyl-4,9-dihydro-1H-napth (2,3-d)imidazol-4,9-imine is obtained from N-methylisoindole and the hetaryne generated in situ from 5-chloro-1-methylimidazole. The crude product is purified by column chromatography on silica gel.

When the N-methylisoindole of Example 8 is replaced by an equivalent amount of 1,2,3-trimethylisoindole; 2-cyclopropyl-1,3-dimethylisoindole; and 2-(3-hydroxypropyl)-1,3-dimethylisoindole, respectively, there is obtained 1,4,9,10-tetramethyl-4,9-dihydro-1H-naphth[2,3-d]-imidazol-4,9-imine; 1,4,9-trimethyl-10-cyclopropyl-4,9-dihydro-1H-naphth[2,3-d]-imidazol-4,9-imine; and 1,4,9-trimethyl-10-(3-hydroxypropyl)-4,9-dihydro-1H-naphth[2,3-d]-imidazol-4,9-imine, respectively.

EXAMPLE 9

6,11,13-Trimethyl-6,11-dihydro-5-azanaphthacen-6,11-imine

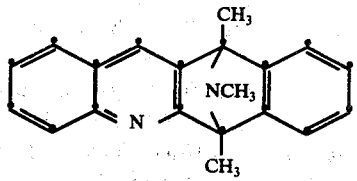

Following the procedure described in Example 3, 6, 11, 13-trimethyl-6,11-dihydro-5-azanaphthacen-6,11-imine is obtained from 1,2,3-trimethylisoindole and the hetaryne generated in situ from 3-bromo-2-chloroquinoline. the crude product is purified by column chromatography.

EXAMPLE 10

1,12,13-Trimethyl-7,12-dihydrobenzo(j)phenanthridin-7,12-imine

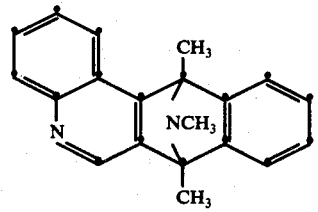

Following the procedure described in Example 3, 7,12,13-trimethyl-7,12-dihydrobenzo (j)phenanthridin-7,12-imine is obtained from 1,2,3-trimethylisoindole and the hetaryne generated in situ from 3-bromo-4-chloroquinoline. The purified product is isolated by column chromatography.

EXAMPLE 11

13-Methyl-7,12-dihydrobenzo(b)phenanthridin-7,12-imine

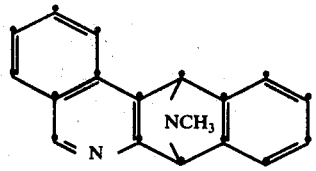

Following the procedure described in Example 7, 13-methyl-7,12-dihydrobenzo(b)phenanthridin-7,12-imine is obtained from N-methylisoindole and the hetaryne generated in situ from 4-bromoisoquinoline. The purified product is isolated by Column chromatography.

EXAMPLE 12

13-Methyl-5,12-dihydronaphtho(3,2-C)(1,5)naphthyridin-5,12-imine

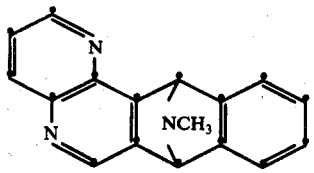

Following the procedure described in Example 7, 13-methyl-5,12-dihydronaphtho(3,2-C)-naphthyridin-5,12-imine is obtained from N-methylisoindole and the hetaryne generated in situ from 4-bromo-1,5-naphthyridine. The purified product is isolated by column chromatography.

EXAMPLE 13

Preparation of intravenous solutions

A solution containing 10 mg. of 1-aza-5,10-dihydro-5,10,11-trimethylanthracen-5,10-imine hydrogen oxalate per ml. of injectable solution is prepared in the following manner.

A mixture of 10 mg. of 1-aza-5,10-dihydro-5,10,11-trimethylanthracen-5,10-imine hydrogen oxalate and 9 mg. of sodium chloride is dissolved in sufficient water for injection to make 1 ml. of solution. The pH is adjusted using hydrochloric acid or aqueous sodium hydroxide to about pH 7.0.

If it is desired that the intravenous solution be used for multi-dose purposes, 1.0 mg. of methyl-p-hydroxy-benzoate (methyl paraben) and 0.10 mg. of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg., respectively, of 1-aza-5,10-dihydro-5,10,11-trimethylanthracen-5,10-imine hydrogen oxalate per ml. of solution are similarly prepared substituting the indicated amount for the above-illustrated 10 mg. quantity. Bulk injectable solutions of convenient volume for subsequent delivery in unit dosage form are readily prepared following the same procedure.

Following the procedure of Example 13 other representative injectable solution of the present invention are prepared when the 1-aza-5,10-dihydro-5,10,11-trimethylanthracen-5,10-imine hydrogen oxalate of Example 13 is replaced by an equivalent amount of 1-aza-5,10dihydro-11-methylanthracen-5,10-imine difumarate or by an equivalent amount of any of the heterocyclic anthracenimine of the present invention illustrated in the foregoing Examples.

EXAMPLE 14

Tablet Preparation

Tablets containing 1.0, 2.0, 25.0, 26.0, 50.0 and 100.0 mg., respectively of 1-aza-5,10-dihydro-5,10,11-trimethylanthracen-5,10-imine hydrogen oxalate are prepared as illustrated below.

| TABLET FOR DOSES CONTAINING FROM 1-25 MG. OF THE HETEROCYCLIC ANTHRACENIMINE COMPOUND | | | |
|---|---|---|---|
| | Amount — mg. | | |
| 1-Aza-5,10-dihydro-5,10,11-trimethylanthracen-5,10-imine hydrogen oxalate | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG. OF THE HETEROCYCLIC ANTHRACENIMINE COMPOUND | | | |
|---|---|---|---|
| | Amount — mg. | | |
| 1-Aza-5,10-dihydro-5,10,11-trimethylanthracen-5,10-imine hydrogen oxalate | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | .39 | 0.75 | 1.5 |

All of the 1-aza-5,10-dihydro-5,10,11-trimethylanthracen-5,10-imine hydrogen oxalate, lactose and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg., 2.0 mg., 25.0 mg., 26.0 mg., 50.0 mg., and 100.0 mg. of 1-aza-5,10-dihydro-5,10,11-trimethylanthracen-5,10imine hydrogen oxalate per tablet.

Following the procedure of Example 14 tablets comprising 1-aza-1,50-dihydro-11-methylanthracen-5,10-imine difumarate are prepared when the 1-aza-5,10-dihydro-5,10,11-trimethylanthracen-5,10-imine hydrogen oxalate of Example 13 is replaced by an equivalent amount of 1-aza-5,10-dihydro-11-methylanthracen-5,10-imine difumarate. Other tablets are prepared using the same procedures and the equivalent amounts of excipients along with equivalent amounts of the heterocyclic anthracenimine compounds of the present invention prepared in accordance with the procedures of the foregoing Examples.

What is claimed is:

1. A compound selected from the group consisting of:

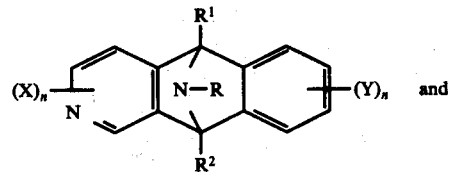 and

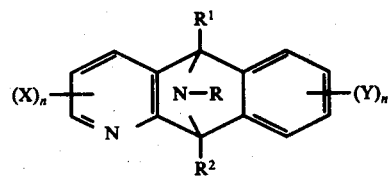

wherein
$R^1$ and $R^2$ are selected from the group consisting of hydrogen, lower alkyl having from 1 to 6 carbon atoms, trifluoromethylsulfonyl, trifluoromethyl, dimethylaminopropyl;

R is hydrogen or lower alkyl having from 1 to 6 carbon atoms, benzyl, dimethylaminopropyl, cyclopropyl, or cyclobutyl;

X and Y are iodo, chloro, bromo, lower alkoxy having from 1 to 6 carbon atoms, lower alkyl having from 1 to 6 carbon atoms, thiomethyl, carboxamido, trifluoromethoxy, trifluoromethyl, trifluoromethylsulfonyl, and trifluoromethylthio;

n is an integer selected from 0 (X or Y is hydrogen), and 1.

2. A method of producing a tranquilizing, muscle relaxant, anticonvulsant and/or anti-Parkinson effect in a patient in need of such treatment by the administration of an effective amount of a compound of formula:

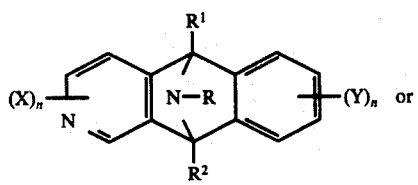

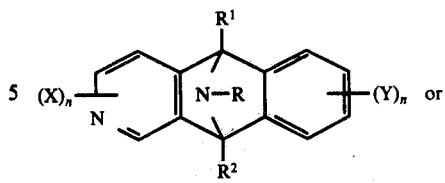

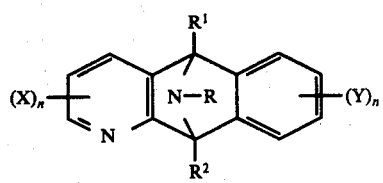

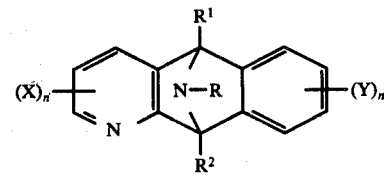

wherein
R[1] and R[2] are selected from the group consisting of hydrogen, lower alkyl having from 1 to 6 carbon atoms, trifluoromethylsulfonyl, trifluoromethyl, dimethylaminopropyl;

R is hydrogen or lower alkyl having from 1 to 6 carbon atoms, benzyl, dimethylaminopropyl, cyclopropyl, or cyclobutyl;

X and Y are iodo, chloro, bromo, lower alkoxy having from 1 to 6 carbon atoms, lower alkyl having from 1 to 6 carbon atoms, thiomethyl, carboxamido, trifluoromethoxy, trifluoromethyl, trifluoromethylsulfonyl, and trifluoromethylthio;

n is an integer selected from 0 (X or Y is hydrogen), and 1.

3. A pharmaceutical composition for use as tranquilizer, muscle relaxant, anti-convulsant and/or anti-Parkinson agent in unit dosage form comprising a pharamaceutical carrier and an effective amount of a compound of formula:

wherein
R[1] and R[2] are selected from the group consisting of hydrogen, lower alkyl having from 1 to 6 carbon atoms, trifluoromethylsulfonyl, trifluoromethyl, dimethylaminopropyl;

R is hydrogen or lower alkyl having from 1 to 6 carbon atoms, benzyl, dimethylaminopropyl, cyclopropyl, or cyclobutyl;

X and Y are iodo, chloro, bromo, lower alkoxy having from 1 to 6 carbon atoms, lower alkyl having from 1 to 6 carbon atoms, thiomethyl, carboxamido, trifluoromethoxy, trifluoromethyl, trifluoromethylsulfonyl, and trifluoromethylthio;

n is an integer selected from 0 (X or Y is hydrogen), and 1.

4. The compound 1-aza-5,10-dihydro-11-methylanthracen-5,10-imine.

5. The compound, 2-aza-5,10-dihydro-11-methylanthracen-5,10-imine.

6. The compound, 2-aza-5,10-dihydro-5,10,11-trimethylanthracen-5,10-imine.

7. The compound, 1-aza-5,10-dihydro-5,10,11-trimethylanthracen-5,10-imine.

* * * * *